United States Patent [19]

Gianna et al.

[11] Patent Number: 5,021,338

[45] Date of Patent: Jun. 4, 1991

[54] ENZYME EXTRACT FROM GERMINATED SORGHUM FOR HYDROLYSIS OF PROTEIN MATERIAL

[75] Inventors: Roberto Gianna; Enrico De Gregoriis, both of Rome; Renzo Boni, Castelnuovo Di Porto, all of Italy

[73] Assignees: Eniricerche S.p.A., Milan; Enichem Synthesis S.p.A., Palermo, both of Italy

[21] Appl. No.: 285,668

[22] Filed: Dec. 16, 1988

[30] Foreign Application Priority Data

Dec. 18, 1987 [IT] Italy ............................ 23084 A/87

[51] Int. Cl.$^5$ ....................... C12P 21/06; C12N 9/50; A23J 3/00; A61K 37/02
[52] U.S. Cl. ................................. 435/68.1; 435/219; 426/47; 426/49; 426/52; 530/343
[58] Field of Search ................. 435/68.1, 219; 426/47, 426/49; 530/52

[56] References Cited

U.S. PATENT DOCUMENTS 3,857,966  12/1974  Feldman et al. ............... 426/49 X
4,452,888  6/1984   Yamazaki et al. ............. 435/68.1

OTHER PUBLICATIONS

Garg et al., Eur. J. Biochem., vol. 17, No. 1, 1970, pp. 4–12, 13–18.

*Primary Examiner*—David M. Naff
*Attorney, Agent, or Firm*—Oblon, Spivak, McClelland, Maier & Neustadt

[57] ABSTRACT

An enzyme system for hydrolysis of protein material from plant and animal sources is obtained by extracting germinated sorghum seeds. The enzyme system contains a proteolytic component active on intact proteins and large peptides at an optimum pH of 3.2 to 4.2 and a peptidase component active on small peptides at an optimum pH of 4.5 to 6.5. A protein hydrolyzate having an average molecular weight within a selected range can be obtained by varying the pH so as to depress activity of the proteolytic component or the peptidase component. The protein hydrolysates which are obtained are characterized by the absence of bitter taste. Furthermore, by suitably adjusting the enzyme concentration in the reaction medium, the temperature and the hydrolysis time, protein hydrolyzates with an average molecular weight lower than 700 and a low percentage of free amino acids can be obtained.

16 Claims, No Drawings

ENZYME EXTRACT FROM GERMINATED SORGHUM FOR HYDROLYSIS OF PROTEIN MATERIAL

The present invention refers to a new method for the production of protein hydrolyzates by means of a particular enzyme system obtained from a plant source and to the thus obtained protein hydrolyzates. In particular, a first object of the present invention is a process for the enzymatic hydrolysis of proteinaceous material from plant or animal sources, using an enzyme system obtained through extraction of germinated sorghum seeds.

A second object of the present invention is the thus obtained protein hydrolyzate which can be employed in the field of nutrition.

Protein hydrolyzates are in general mixtures of polypeptides with different molecular weights, obtained through hydrolysis, either enzymatic or chemical, of natural proteinaceous material.

Said hydrolyzates are often used in the food industry to enhance the nutritional value of the low protein food products they are added to.

For the use as food additives, these hydrolyzates must have some specific properties: they must be soluble and/or dispersible at the pH of the food product they are added to (for instance, to be used for the preparation of high-protein beverages, said hydrolyzates must be soluble at acidic pH) and have an acceptable taste. This last point creates particular problems, as generally, protein hydrolyzates, both from plant or animal sources, share a characteristic bitter taste which cannot be masked by the addition of flavouring or sweetening agents.

Furthermore, for some particular applications in the field of nutrition (nutrition of wasted children or of adults with gastro-enteric pathologies), low molecular weight protein hydrolyzates, typically with an average molecular weight lower than 700, are preferred because they are more easily uptaken.

Additionally, said low molecular weight protein hydrolyzates should also contain a low percentage (lower than 20%) of free amino acids, as the uptake from the intestinal wall mainly occurs with small peptides (2–5 amino acids) which are then hydrolyzed to free amino acids by the endogenous peptidases, rather than with free amino acids as such.

In this connection, processes for the enzymatic hydrolysis of proteinaceous material to afford low molecular weight protein hydrolyzates with a low content of free amino acids, are described in the open and patent literature (see for instance EP-A-0044032). In the known processes, however, this result is achieved by employing at least two different proteases. The enzymatic hydrolysis according to the present invention, on the other hand, affords protein hydrolyzates completely free from bitterness and makes it possible, by suitably adjusting the hydrolysis conditions (concentration of the enzyme system, hydrolysis temperature and time) to get low molecular weight protein hydrolyzates with a low content of free amino acids, using a single enzyme system.

In particular, the enzymatic hydrolysis according to the present invention is carried out using as the enzyme system a protein extract from germinated sorghum seeds.

It has been noticed in fact that by germinating sorghum seeds of different varieties for a few days (at least two days), the enzyme extract which is obtained therefrom is capable of hydrolysing both high molecular weight proteins and lower molecular weight polypeptides, affording a protein hydrolyzate completely free from bitterness that, depending on the hydrolysis conditions, may have an average molecular weight even lower than 700.

The process for obtaining said enzyme extract from the germinated seeds is a conventional one and can be summarized as follows:

the germinated sorghum seeds are homogenized, the undesired organic substances, e.g. tannins which impart a bitter taste and a dark brown color to the homogenized material, are removed therefrom by washing it with an organic solvent, typically acetone, the enzyme fraction is then extracted from the solid residue by means of an almost neutral buffer, typically a phosphate buffer, and the enzyme fraction is then salted out from the buffer solution by the addition of inert salts, typically ammonium sulphate, to saturation.

Said precipitation may also be carried out in the presence of an organic solvent, thus layering the enzyme fraction between the salted solution and the organic solvent.

The isolation and purification up to a homogeneous product of an acid protease from germinated sorghum seeds is described in literature (G. K. Garg and T. K. Virupaksha—Eur. J. Biochem., 17, (1970), pages 4–12) as well as the characterization of the thus purified enzyme (G. K. Garg and T. K. Virupaksha—Eur. J. Biochem., 17, (1970), pages 13–18).

The enzyme purified by DEAE-cellulose chromatography, which is characterized in the above quoted reference by a specific activity of 600 units/mg of protein/h, is there defined as an endopeptidase that specifically cleaves the peptide linkages involving the -carboxyl group of the aspartic and glutamic acids. Just owing to its narrow specificity, the possible uses of said endopeptidase in protein sequencing studies have been mainly investigated. The subsequent studies (see for instance T. K. Virupaksha and K. Wallenfels in FEBS Letters, Vol. 40(2), 1974, pages 287–9), therefore, have been aimed at developing simple and rapid procedures for its careful purification.

It has now surprisingly been found that the enzyme fraction which can be obtained from germinated sorghum seeds, simply by extraction (thus before any purification step), actually consists of two different activities, a proteolytic component, active on intact proteins and large peptides, and a peptidase component, active on small peptides, and that the use of such system in the enzymatic hydrolysis of protein material from plant or animal sources, leads to protein hydrolyzates completely free from any bitter taste.

It has been found, furthermore, that the optimum pH of the proteolytic activity varies between 3.2–4.2 and preferably between 3.5–3.9, while the optimum pH of the peptidase activity is higher, varying between 4.5–6.5 and preferably between 5.2–6.2, and that therefore, depending on the pH of hydrolysis, it is possible to depress one of the two activities, favouring the other. Protein hydrolyzates with an average molecular weight within a suitably selected range can therefore be obtained.

In particular, the presence of both types of activities allows to use said enzyme system in the production of low molecular weight protein hydrolyzates.

In this case, the hydrolytic treatment can be started at a pH which is more suitable for the expression of the proteolytic activity (3.5–3.9) without controlling it; expression of the proteolytic activity does occur first, with a consequent increase in pH, followed by the predominant expression of the peptidase activity. Unlike other enzyme systems from microbial sources (EP-A-0044032) or other types of enzyme systems obtained by extracting procedures, no toxicity problems are obviously involved in the use of the raw enzyme extract of the present invention, as it is derived from seeds which have been used for many centuries in the field of nutrition and whose safety has already been confirmed.

The enzyme system according to the present invention may be employed in the hydrolysis of protein material from plant as well as animal sources. In particular, starting protein materials which can be used in the process of the present invention are soya, sunflower, cotton, milk, egg, and the like protein products, with a protein content which generally ranges from 50 to 95%.

The enzymatic hydrolysis according to the present invention is actually carried out by dispersing the protein material in water, adjusting the pH of the dispersion to a value of from 3.0 to 6.5 and adding the enzyme system thereto.

The substrate concentration in water, expressed as % w/v, will mainly depend on the type of starting material and its solubility and/or dispersability in water at the pH of hydrolysis.

Optimum concentrations range from 2.5 to 20%, even if for some proteins which are particularly soluble in water, higher concentrations could also be employed. Optimum pH also will depend on the type of starting proteinaceous material and on the desired product. As already pointed out, in fact, the two types of activities expressed by the sorghum enzyme extract of the present invention have different optimum pH's and the choice of the initial pH will depend on the size of the starting proteins and on the average molecular weight of the end protein hydrolyzate that is desired. In general, however, starting from intact proteins or large peptides, the optimum initial pH will be from 3.5 to 4.0, while starting from smaller peptides, the optimum pH will preferably range from 5.0 to 6.0.

The pH is adjusted to the desired value by the addition of an inorganic or organic acid e.g. hydrochloric acid, sulphuric acid, citric acid, etc., or by the addition of a base such as, for instance, NaOH, KOH, etc..

The enzyme system is added to the protein dispersion, in a concentration generally ranging between 10 and 100 U/ml and, preferably, between 20 and 60 U/ml.

To determine the proteolytic activity of the enzyme system of the present invention, the method described by G. K. Garg and T. K. Virupaksha in Eur. J. Biochem., 17, (1970), pages 4–12, can be used. Said method comprises adding a predetermined amount of the enzyme system to a 0.125% albumin solution dissolved in 0.05M sodium citrate buffer, pH 3.7, (2 ml), incubating the mixture for 60 minutes at 50° C., stopping the hydrolysis by the addition of 10% trichloroacetic acid (2 ml), separating the supernatant by centrifugation, and determining the concentration of the hydrolyzed protein by the Anson method (M. L. Anson et al., J. Gen. Physiol., (1933), 16, page 59). One unit of enzyme proteolytic activity is then defined as the amount which releases 10 $\mu$g of tyrosine under the conditions of assay.

Enzymatic hydrolysis can be carried out at a temperature ranging from 25 to 60° C., but preferably at a temperature higher than 35° C. and, even more preferably, at a temperature of from 37° to 55° C.

Hydrolysis is generally continued for a period of time of from 4 to 48 hours, depending on the type of product desired.

When enzymatic hydrolysis is carried out using as the starting material a substrate which is poorly soluble in water, such as for instance some soya, caseine or sunflower protein products, the yields are generally low because of the poor accessibility of this material to the proteolytic enzyme.

In order to get a higher hydrolysis yield it is therefore advisable, in this case, to carry out a mild pre-hydrolytic step in neutral or slightly alkaline conditions, conditions wherein the substrate is more soluble in water, and then submitting the thus obtained pre-hydrolizate to hydrolysis with the sorghum enzyme extract. Said pre-hydrolizate in fact, depending on the conditions of the pre-hydrolytic step, has an average molecular weight lower than the starting proteinaceous material and is therefore more soluble in aqueous acidic medium (i.e. more freely accessible to the enzyme).

Another object of the present invention is, therefore, the enzymatic hydrolysis, with the sorghum enzyme extract, of a starting material deriving from an enzymatic pre-hydrolytic step under neutral or slightly alkaline conditions.

The following examples are only aimed at illustrating in more detail some representative embodiments of the present invention and in no way they should be interpreted as a limitation to the scopes thereof.

EXAMPLE 1

Sorghum enzyme extract

Sorghum seeds (*Sorghum vulgare*) of three different varieties (Aralba, F27R, and F30R) have been obtained from Istituto di Cerealicoltura in Rome, and have been separately submitted to the following treatment:

Superficial sterilization

The seeds are treated, after screening, with two volumes of a solution of sodium hypochlorite (8% $Cl_2$), and 2–3 minutes later are washed thoroughly and repeatedly with water. The washed seeds are then treated with 4 volumes of 3% $H_2O_2$, and after 3–4 minutes are washed carefully with water.

Germination

The thus treated seeds are spread over plates (35×40 cm) containing a water soaked filter paper on the bottom and are incubated in the oven for five days, alternating 8 hours at 30° C. to 16 hours at 20 C.

Preparation of the raw extract

The germinated seeds, after five days of incubation, are recovered, treated with two volumes of cold acetone (−10° C.) and homogenized for three minutes at 8000 rpm. After filtration and washing with cold acetone, a white-pinky powder is obtained. This powder is suspended in four volumes of 0.05M sodium phosphate buffer, pH 6.8, and, while keeping the temperature at 4° C., is homogenized for 4 minutes at 10.000 rpm. The mixture is centrifuged and the liquid supernatant containing the enzymatic activity is recovered. This is treated with acetone (30%, v/v) at −5° C., discarding the precipitate which separates upon an additional centrifugation. To the acetone supernatant, ammonium sulphate is added to 55% saturation. An acetone upper phase and a more salty lower phase are thus obtained, and inbetween a protein disc which is recovered after removal of both liquid phases.

Said protein disc is dissolved in phosphate buffer, is dialyzed against the same buffer and then freeze-dried. Following Table I summarizes the characteristics of the enzyme systems obtained from 180 g of sorghum seeds of the above quoted varieties.

TABLE I

| Seed Variety | Overall Units Obtained | Specific Activity (U/mg of prot/h 50 C) |
|---|---|---|
| Aralba | 12500 | 26.2 |
| Aralba | 13900 | 31.0 |
| Aralba | 20110 | 8.0 |
| F-27R | 13200 | 28.0 |
| F-27R | 13050 | 24.6 |
| F-27R | 16070 | 22.0 |
| F-27R | 13050 | 25.7 |

EXAMPLES 2-7

Preparation of protein hydrolyzates

General method

A general method, employed in the following examples, involves dispersion of the substrate in water at a concentration of 4% w/v, adjustment of the pH to the desired value by the addition of 0.1N HCl, and addition of the enzyme system obtained as described in Example 1, to the thus obtained dispersion, in an amount corresponding to 2-6% by weight with respect to the substrate, depending on the specific activity and salt content. The suspension is stirred at 50° C. for the suitably selected time, is then centrifuged and the supernatant is separated and freeze-dried.

The average molecular weight and the molecular weight distribution are determined by the following method: the hydrolyzate average molecular weight ($\overline{MW}$) is determined by using a BioGel® P60 (1.6×60 cm) column equilibrated with 6M guanidine, working with a flow rate of 7 ml/h, collecting 1.9 ml-fractions, and measuring absorbance at 280 nm.

The column is previously calibrated with six proteins and peptides with known molecular weights: 13.800, 6.500, 3.450, 1.450, 1.060, and 451. As for the void volume and the overall volume, seralbumin (MW 64.000) and tryptophan (MW 204) respectively, are employed. The distribution coefficient, $K_{av}$, of each standard is calculated from the relationship $$K_{av} = (V_e - V_o)/(V_t - V_o)$$

wherein $V_o$ is the void volume, $V_t$ is the overall volume, and $V_e$ is the elution volume of each standard. The calculated distribution coefficients $K_{av}$, arranged by decreasing molecular weight, are: 0 (seralbumin), 0.255, 0.377, 0.449, 0.658, 0.694, 0.877 and 1 (tryptophan).

The average molecular weight is calculated by using the equation of Hjerten (J. Chromat. (1970), 50, 189-208). The samples to be chromatographed are dissolved in 0.05M phosphate buffer, pH 7, to a concentration of 40 mg/ml, and maintained at 100° for 10 minutes in order to inactivate and remove the enzyme. The supernatants are recovered by centrifugation, diluted with four volumes of 6M guanidine and charged to the column. The molecular weight distribution and the average molecular weight are then calculated by determining the absorption at 280 nm.

On the other hand, the content of free amino acids has been determined by the Bellinger method (J. Chromat., (1973), 87, 513-22), which uses a resin column, such as BioRad, in racemic form, that selectively retains neutral and basic amino acids, while the acidic amino acids are eluted together with the peptide fraction and quantitated directly and independently, by the Bergmeyer method (H. U. Bergmeyer—Method of enzymatic analysis—(1965)—2nd Edition—381-97). The preparation of the resin in racemic form is achieved by suspending the resin in 20 bed volumes of saturated cupric sulphate solution for 12 hours at 4° C. After washing it carefully with water, until the supernatant shows no copper, the resin is equilibrated with 0.1M NH₄OH and used to pack the column. The sample (10 mg/ml) is brought to pH 10 with NH₄OH and applied to the column. By eluting with 0.1M NH₄OH, the first fraction which is collected contains peptides and free acid amino acids. By increasing then the concentration of the eluent to 2M, the basic and neutral amino acids which had been retained, are eluted. Any complexed copper is then removed by passing this solution through a BioRad-like column in ammonium form. The fractions which are collected are concentrated and carefully washed with alkaline water; the free amino acids and the peptides are determined by the conventional ninhydrin method.

The yield of the hydrolytic process ($\eta$% of hydrolysis) is determined calculating the overall nitrogen content in the starting material and in the recovered hydrolyzate, by the Kjeldhal method. It is expressed as:

$$\eta\% = \frac{\text{Overall Nitrogen in the Hydrolyzate}}{\text{Overall Nitrogen in the Starting Mat.l}} \times 100$$

EXAMPLE 3

Protein hYdrolyzate from intact proteins

Table II below summarizes the characteristics of the protein hydrolyzates obtained with the enzyme system of the present invention starting from different substrates and carrying out the hydrolysis, according to the general method of the preceding example, at pH 3.7 for 23 hours, with 50 U/ml of the enzyme. In Table II, as well as in the other Tables, symbols A, B, C, D, and E, represent protein hydrolyzate fractions characterized by the following molecular weights:

A: from 46.800 to 5.250
B: from 5.250 to 2.200
C: from 2.200 to 1.000
D: from 1.000 to 750, and
E: lower than 750

F represents the % of free amino acids and G the % yield of the hydrolysis ($\eta$% hydr.).

| Substrate and enzyme specific activity (S.A.) | $\overline{MW}$ | % different fractions | | | | | F | G |
|---|---|---|---|---|---|---|---|---|
| | | A | B | C | D | E | | |
| Casein[1] S.A. = 8 | 450 | 0 | 0 | 1 | 4.1 | 94 | 18 | 40 |
| Casein[1] S.A. = 22 | 500 | 0 | 0 | 6.8 | 3.2 | 90 | 18 | 41 |
| Seralbumin S.A. = 8 | 730 | 0 | 9.3 | 6.3 | 2.4 | 82 | 8 | 92 |

-continued

| Substrate and enzyme specific activity (S.A.) | MW | % different fractions | | | | | | |
|---|---|---|---|---|---|---|---|---|
| | | A | B | C | D | E | F | G |
| Soya protein[2] S.A. = 22 | 435 | 0 | 0.5 | 2.3 | 2.5 | 89 | 16 | 38 |

Table III below reports the characteristics of the protein hydrolyzates obtained with the enzyme system of the present invention with specific activity=22, starting from albumin and carrying out the hydrolysis for 6 hours at 50° C., and pH 3.7 or 5.8.

TABLE III

| pH | MW | % different fractions | | | | | | |
|---|---|---|---|---|---|---|---|---|
| | | A | B | C | D | E | F | G |
| 3.7 | 1.530 | 1.7 | 13.1 | 22.6 | 2 | 60.6 | 6.5 | 70 |
| 5.8 | 5.100 | 15.2 | 12 | 12.5 | 6.6 | 53.7 | 28 | 46 |

EXAMPLE 4

Protein hydrolyzates from pre-hydrolyzates

To improve the hydrolytic activity of the enzyme system of the present invention which works at acidic pH's, when the hydrolysis is carried out starting from proteins which are not sufficiently soluble in the acidic medium, such as for instance soya, casein, sunflower, and the like, it is advisable to carry out a pre-hydrolytic treatment in a neutral or slightly alkaline medium where, being soluble, these protein materials can be more easily digested by a suitably selected basic or neutral protease, such as Alcalase or a neutral protease from B.Subtilis.

The method actually employed in the present pre-hydrolytic step involves adding an amount of basic or neutral protease corresponding to 30 U/ml (1% w/v) to a 4% solution of the protein, and incubating at 37° C. for 30–60 minutes while keeping the pH at the optimum value for the protease (pH 8 for the basic protease and pH 7 for the neutral protease) by the addition of 0.5N NaOH. The enzyme is then inactivated by adjusting the pH to 4.0 by the addition of 0.5N HCl and heating to 100° C. for 10 minutes. Generally, the obtained pre-hydrolyzates are almost completely soluble in the pH range suitable for the sorghum enzyme extract.

As an example in following Table IV the characteristics of intact casein and of casein pre-hydrolyzates with alcalase or a neutral protease from Bacillus subtilis, are reported.

TABLE IV

| Substrate | MW | % different fractions | | | | | |
|---|---|---|---|---|---|---|---|
| | | A | B | C | D | E | F |
| Intact Casein | 34.500 | 100 | 0 | 0 | 0 | 0 | 0 |
| Casein pre-hydr. alcalase | 8.600 | 23.8 | 22.6 | 19.1 | 9.7 | 27 | 0.2 |
| Casein pre-hydr. neutral protease | 7.600 | 24.9 | 12.1 | 17.0 | 27.0 | 21 | 0.2 |

Table V below reports the characteristics of the protein hydrolyzates obtained starting from casein pre-hydrolyzed with alcalase, and carrying out the hydrolysis with the sorghum enzyme extract with specific activity 8 U/mg of protein/h at a concentration of 30 U/ml, at 50° C., for 6 or 23 hours, and pH 3.7 or 5.8.

TABLE V

| pH | time (H) | MW | % different fractions | | | | | | |
|---|---|---|---|---|---|---|---|---|---|
| | | | A | B | C | D | E | F | G |
| 3.7 | 6 | 1.350 | 4.6 | 13.4 | 14.8 | 10 | 57 | 4 | 52 |
| 3.7 | 23 | 860 | 0 | 7.1 | 12.4 | 13 | 67 | 10 | 77 |
| 5.8 | 6 | 1.020 | 1.1 | 5.1 | 9.7 | 10.1 | 74 | 9 | 84 |
| 5.8 | 23 | 500 | 0 | 0 | 1.5 | 5.4 | 93 | 18 | 92 |

Analogously, by carrying out the enzymatic hydrolysis with the sorghum enzyme under the same conditions but starting from casein pre-hydrolyzed with a neutral protease, protein hydrolyzates with the characteristics summarized in Table VI below are obtained

TABLE VI

| pH | time (h) | MW | % different fractions | | | | | | |
|---|---|---|---|---|---|---|---|---|---|
| | | | A | B | C | D | E | F | G |
| 3.7 | 6 | 1.330 | 4.6 | 12 | 14.3 | 6.5 | 62.6 | 7 | 61 |
| 3.7 | 23 | 760 | 0 | 0.1 | 6.5 | 4.4 | 89 | 15 | 78 |
| 5.8 | 6 | 1.050 | 1.5 | 14.7 | 13.9 | 5.7 | 63.9 | 8 | 72 |
| 5.8 | 23 | 510 | 0 | 1 | 3.7 | 5.5 | 90 | 12 | 94 |

EXAMPLE 5

Effects of enzyme concentration

The effects of enzyme concentration on the characteristics of the product obtained starting from casein pre-hydrolyzed with alcalase, have been investigated.

Three different concentrations (20, 30, and 50 U/ml) of the enzyme system with a specific activity of 8 U/mg, have been used. Hydrolysis with the sorghum enzyme extract has been carried out at 50° C. and pH 3.7 for 23 hours.

The results are reported in following Table VII

TABLE VII

| Enzyme conc. | MW | % different fractions | | | | | | |
|---|---|---|---|---|---|---|---|---|
| | | A | B | C | D | E | F | G |
| — | 8.600 | 23.8 | 22.6 | 19.1 | 9.7 | 27 | 0.2 | |
| 20 U/ml | 1.370 | 4.6 | 13.4 | 14.8 | 10 | 57 | 4 | 46 |
| 30 U/ml | 860 | 0 | 7.1 | 12.4 | 13 | 67 | 6 | 74 |
| 50 U/ml | 520 | 0 | 1.0 | 5.9 | 5.5 | 85 | 11 | 90 |

EXAMPLE 8

Effect of hydrolysis time

Starting from a soya isolate and from casein, both pre-hydrolyzed with alcalase, the effect of hydrolysis time on the characteristics of the obtained products has been investigated. The hydrolysis has been carried out, at 50° C. and pH 3.7, for 2, 6, or 23 hours, with a concentration of the enzyme system (specific activity of 22 U/mg), of 30 U/ml. The results are reported in following Table VIII

TABLE VIII

| Hydrol. time | MW | % different fractions | | | | | | |
|---|---|---|---|---|---|---|---|---|
| | | A | B | C | D | E | F | G |
| SOYA ISOLATE | | | | | | | | |
| — | 9.200 | 24.8 | 23 | 16.7 | 9.5 | 26 | 0.2 | — |
| 2 h | 3.400 | 15.1 | 17.9 | 15.1 | 5.7 | 46.2 | 1.2 | 41 |
| 6 h | 1.200 | 2.2 | 14.4 | 13.8 | 4.2 | 65.4 | 5.5 | 64 |
| 23 h | 540 | 0 | 0 | 3.2 | 2.2 | 94 | 18.2 | 91 |
| CASEIN | | | | | | | | |
| — | 8.600 | 23.8 | 22.6 | 19.1 | 9.7 | 27 | 0.2 | — |
| 2 h | 3.200 | 14.7 | 18.3 | 14.1 | 5.3 | 48 | 1.6 | 48 |

TABLE VIII-continued

| Hydrol. time | $\overline{MW}$ | % different fractions | | | | | | |
|---|---|---|---|---|---|---|---|---|
| | | A | B | C | D | E | F | G |
| 6 h | 1.050 | 1.5 | 14.7 | 13.5 | 5.2 | 65 | 5.4 | 62 |
| 23 h | 690 | 0 | 7.0 | 8.8 | 3.7 | 80 | 15 | 80 |

To confirm the merit of the enzyme system of the present invention with respect to other microbial proteases commonly employed, one of the above substrates, namely casein pre-hydrolyzed with alcalase, is treated with a commercially available protease from *Aspergillus niger*, and the hydrolysis is carried out in the optimum conditions taught by the literature for said protease (pH 3.0, 50° C., 3% (w/w) enzyme/substrate), and 6 and 23 hours with the results reported in Table IX

TABLE IX

| Hydrolysis time | $\overline{MW}$ | % E fraction |
|---|---|---|
| 6 h | >1500 | 63 |
| 23 h | >1500 | 67 |

EXAMPLE 7

Effect of enzyme specific activity

Tests have been carried out starting from casein (4%) pre-hydrolyzed with alcalase, incubating it for 23 hours at 50° C. and pH 3.7, with 30 U/ml of samples of the enzyme system from three different preparations (Example 1) with specific activity 8, 22, and 31. Furthermore, for comparison purposes, a sorghum protease purified by affinity chromatography on bacitracin as described in J.Appl. Biochem., 5, 420–28, (1983), with a specific activity of 185 and devoid of peptidase activity, has also been employed. The results are summarized in following Table X

TABLE X

| S.A. | $\overline{MW}$ | % different fractions | | | | | | |
|---|---|---|---|---|---|---|---|---|
| | | A | B | C | D | E | F | G |
| 8 | 590 | 0 | 2.1 | 2.8 | 8.3 | 84 | 16 | 75 |
| 22 | 690 | 0 | 7.0 | 8.8 | 3.7 | 80 | 15 | 80 |
| 31 | 530 | 0 | 1.0 | 6.0 | 5.0 | 85 | 11 | 80 |
| 185 | 1330 | 0 | 19 | 13 | 8 | 56 | 8 | 65 |

These data show that the specific activity does not influence the average molecular weight of the hydrolyzate provided however that the two types of activities (proteolytic and peptidase) are not separated as it is shown by the fact that the known purified enzyme with specific activity 185, without the peptidase component, is not capable of providing a low molecular weight hydrolyzate.

As anticipated the protein hydrolyzates obtained by the process of the present invention are completely free from bitterness.

In particular an organoleptic assay of the following protein hydrolyzates has been carried out:

1 - soya hydrolyzate with an average molecular weight of 1.200, obtained according to the process of Example 6, by carrying out the hydrolysis for 6 hours;
2 - soya hydrolyzate with an average molecular weight of 540, obtained according to the process of Example 6, continuing the hydrolysis for 23 hours;
3 - casein hydrolyzate with an average molecular weight of 1.050, obtained by the process of Example 6 continuing the hydrolysis for 6 hours;
4 - casein hydrolyzate with an average molecular weight of 690, obtained by the process of Example 6, continuing the hydrolysis for 23 hours;
5 - seralbumin hydrolyzate with an average molecular weight of 730, obtained by the process of Example 2 (Table II);

Hydrolyzate 1 has been compared with two commercial products, consisting of soya hydrolyzates with average molecular weights of 1.540 (6) and 1.380 (7), respectively.

Hydrolyzate 3 has been compared with the following three hydrolyzates:

8 - casein hydrolyzate with a molecular weight of 1.140, obtained by enzymatic hydrolysis of the same starting material of hydrolyzate 3, with alcalase;
9 - casein hydrolyzate with an average molecular weight of 1.280, obtained by enzymatic hydrolysis of the same starting material of hydrolyzate 3, with neutrase;
10 - casein hydrolyzate with an average molecular weight of 1.500, obtained by enzymatic hydrolysis of the same starting material of hydrolyzate 3, with a neutral protease from *Aspergillus niger*;

As far as hydrolyzates 2,4 and 5 are concerned, it has not been possible to carry out an organoleptic comparative test because there are no equivalent protein hydrolyzates obtained with different enzyme systems.

The organoleptic analysis has been performed by a group of 20 tasters, 25 to 50 years old.

Hydrolyzates 1, 2, 6, and 7, have been tasted in three different formulations:

Formulation A: 5% (w/v) solution in tap water;
Formulation B: 5% (w/v) solution in a 10% (w/v) saccharose solution containing natural orange flavour (0.15% s/v);
Formulation C: 5% (w/v) solution in a 10% (s/v) saccharose solution containing citric acid (0.25% w/v) and natural orange flavour (0.15%);

Protein hydrolyzates 3, 4, 5, 8, 9, and 10 have been tasted only as Formulation A.

The obtained results are reported in following Table XI

TABLE XI

| Hydrolyz. | Formul. | Number of persons who tasted | | |
|---|---|---|---|---|
| | | SB | B | NB |
| 1 | A | 0 | 0 | 20 |
| 1 | B | 0 | 0 | 20 |
| 1 | C | 0 | 0 | 20 |
| 6 | A | 4 | 16 | 0 |
| 6 | B | 5 | 15 | 0 |
| 6 | C | 4 | 16 | 0 |
| 7 | A | 16 | 4 | 0 |
| 7 | B | 14 | 6 | 0 |
| 7 | C | 12 | 8 | 0 |
| 2 | A | 0 | 0 | 20 |
| 2 | B | 0 | 0 | 20 |
| 2 | C | 0 | 0 | 20 |
| 3 | A | 0 | 0 | 20 |
| 8 | A | 3 | 15 | 2 |
| 9 | A | 6 | 14 | 0 |
| 10 | A | 0 | 4 | 16 |
| 4 | A | 0 | 0 | 20 |
| 5 | A | 0 | 0 | 20 |

(SB = strongly bitter taste; B = bitter taste; NB = no bitter taste)

We claims:

1. A process for preparing a protein hydrolyzate, which comprises subjecting a protein material from plant or animal sources to enzymatic hydrolysis at a pH of from about 3.0 to 6.5 with an enzyme extract from germinated sorghum seeds and recovering said protein hydrolyzate, said enzyme extract containing an enzyme system comprising a proteolytic component active on intact proteins and large peptides at an optimum pH of 3.2 to 4.2 and a peptidase component active on small peptides at an optimum pH of 4.5 to 6.5, whereby a protein hydrolyzate having an average molecular weight within a selected range can be obtained by varying the pH so as to depress activity of the proteolytic component or the peptidase component.

2. The process of claim 1, wherein the enzyme extract is obtained by:
   (a) homogenizing germinated sorghum seeds to produce an homogenized material,
   (b) washing said homgenized material with an organic solvent,
   (c) extracting an enzyme fraction therefrom with a neutral aqueous buffer, and
   (d) precipitating the enzyme fraction from the buffer solution by the addition of salts.

3. The process of claim 1, wherein the pH hydrolysis is from 3.2 to 4.2.

4. The process of claim 3, wherein said hydrolysis is from 3.2 to 3.9.

5. The process of claim 1, wherein said pH of hydrolysis is from 4.5 to 6.5.

6. The process of claim 5, wherein said pH of hydrolysis is from 5.2 to 6.2.

7. The process of claim 1, wherein the enzyme system concentration is from 10 to 100 U/ml.

8. The process of claim 7, wherein the enzyme system concentration is from 20 to 60 U/ml.

9. The process of claim 1, wherein hydrolysis is effected for a period of time of from 4 to 48 hours.

10. The process of claim 1, wherein the enzymatic hydrolysis is carried out at a temperature of from 25 to 60° C.

11. The process of claim 10, wherein said hydrolysis is effected at a temperature of from 37° to 55° C.

12. The process of claim 1, wherein said starting protein material is subjected to a mild enzymatic prehydrolysis in neutral or alkaline conditions, before being hydrolyzed with the sorghum enzyme extract.

13. The process of claim 1, wherein said protein material contains a protein content of from 50 to 95% and is obtained from a plant or animal source selected from the group consisting of soya, sunflower, cotton, milk and egg.

14. The process of claim 1, wherein said protein hydrolyzate has an average molecular weight of lower than 700.

15. The process of claim 1, wherein said protein hydrolyzate has a free amino acid content of lower than 20%.

16. The process of claim 1, wherein said protein material from said plant or animal source is present in the amount of about 1.5 to 20% w/v in water for said enzymatic hydrolysis.

* * * * *